United States Patent [19]
Thogho et al.

[11] Patent Number: 5,382,356
[45] Date of Patent: Jan. 17, 1995

[54] METHOD AND APPARATUS FOR CONTROLLING SLUDGE DEWATERING

[75] Inventors: Makoto Thogho; Tamotsu Hattori; Noboru Okazaki, all of Tokyo; Kozaburo Akamatus, Chiba; Tomoyuki Hayashi; Tomohiko Kusumi, both of Saitama, all of Japan

[73] Assignees: Tokyo Metropolitan; Tokyo Metropolitan Sewerage Service Corp.; Japan Organo Co., Ltd., Tokyo, Japan

[21] Appl. No.: 896,439

[22] Filed: Jun. 10, 1992

[30] Foreign Application Priority Data
Nov. 29, 1991 [JP] Japan .................................. 3-316635
Mar. 2, 1992 [JP] Japan .................................. 4-044628

[51] Int. Cl.$^6$ ...................... B01D 21/30; C02F 11/14
[52] U.S. Cl. .................................. 210/96.1; 210/143; 210/149; 210/709; 210/742; 210/746
[58] Field of Search .................. 210/96.1, 709, 739, 210/745, 143, 198.1, 149, 742, 746

[56] References Cited

U.S. PATENT DOCUMENTS
| | | | |
|---|---|---|---|
| 3,393,149 | 7/1968 | Conley et al. | 210/709 |
| 4,396,513 | 8/1983 | Haldeman | 210/734 |
| 5,000,860 | 3/1991 | Drewry | 210/721 |

FOREIGN PATENT DOCUMENTS
| | | |
|---|---|---|
| 79600 | 5/1983 | Japan . |
| 268399 | 11/1986 | Japan . |
| 169398 | 7/1991 | Japan . |

Primary Examiner—Neil McCarthy
Attorney, Agent, or Firm—Cushman, Darby & Cushman

[57] ABSTRACT

The feature of the present invention resides in that when a polyelectrolyte coagulant is added to sludge to dewater the sludge in a sewage treatment plant, the dosage level of the polyelectrolyte coagulant to be to the sludge is controlled most properly, whereby moisture content of dewatered cake can be minimized. This control can be achieved by feeding the coagulant to a sludge feed pipe (3) by means of a coagulant feed pump (6) to carry out a coagulation reaction, dewatering tie sludge by a dewatering means (4), measuring a capillary suction time (CST) of the resultant filtrate (8) by a CST measuring means (10), and then controlling the addition of the coagulant by the coagulant pump (6) so that the filtrate CST value may be minimized 2 Claims, 14 Drawing Sheets

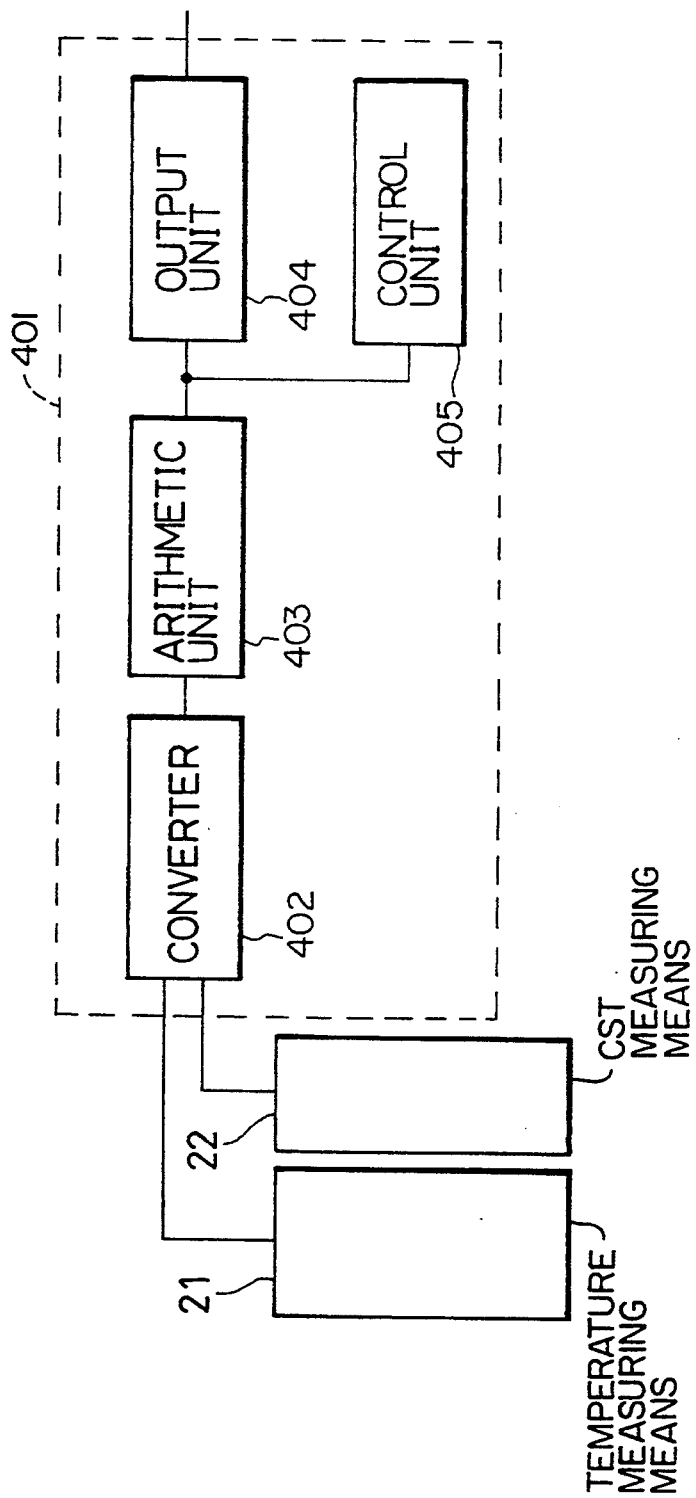

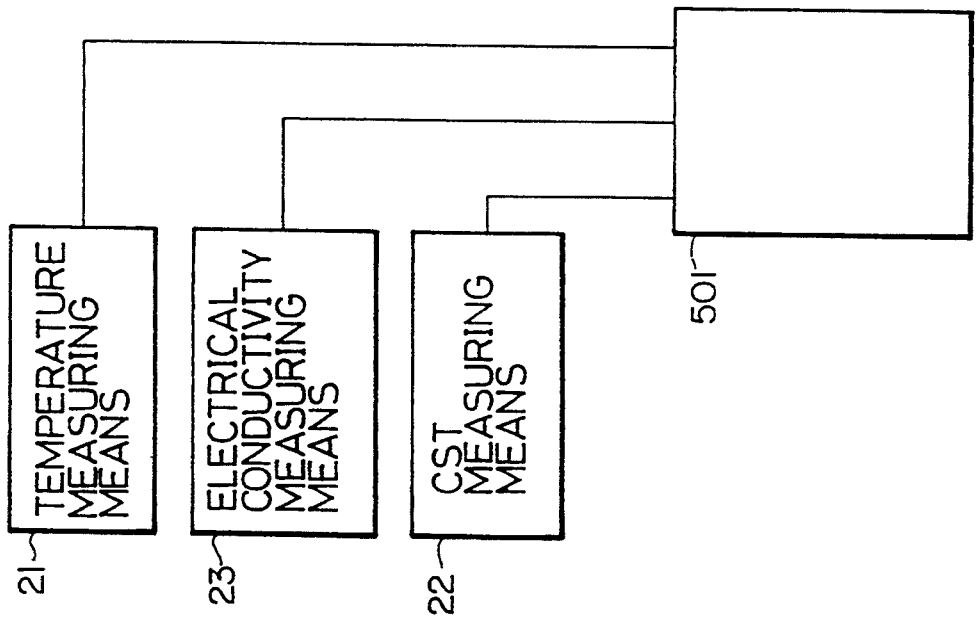
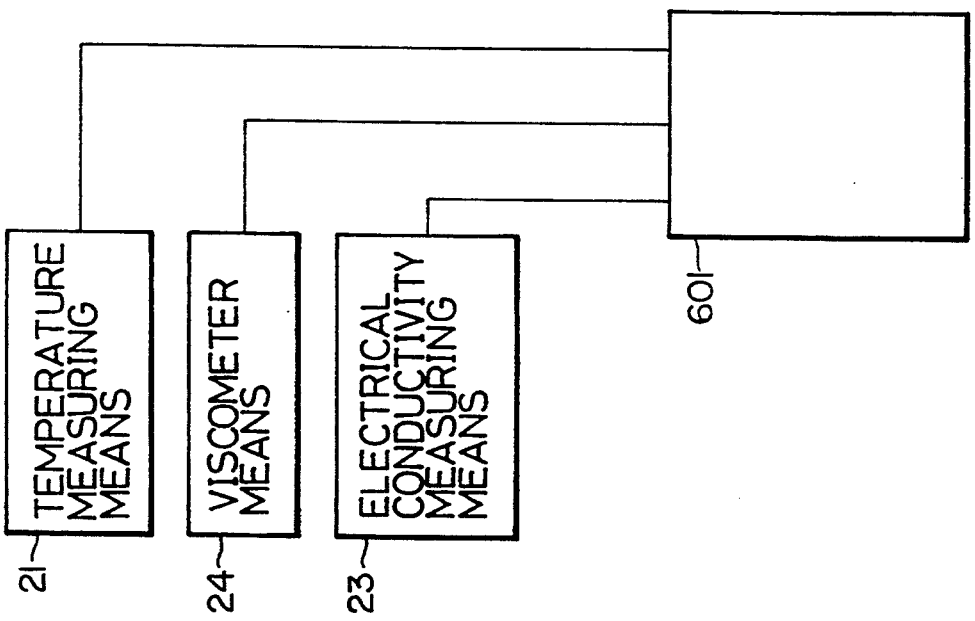

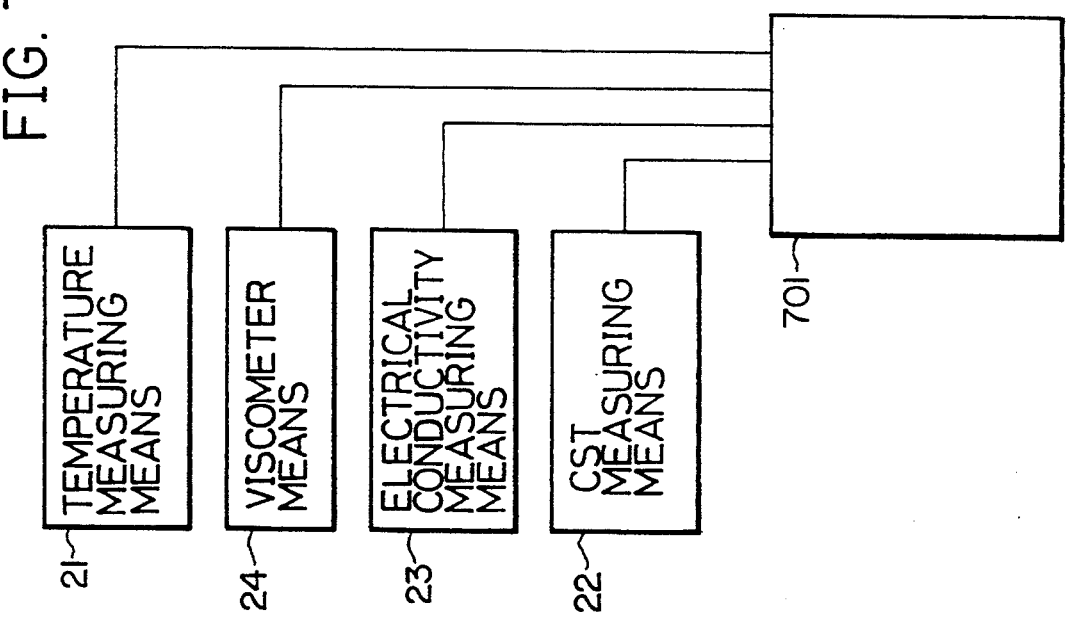

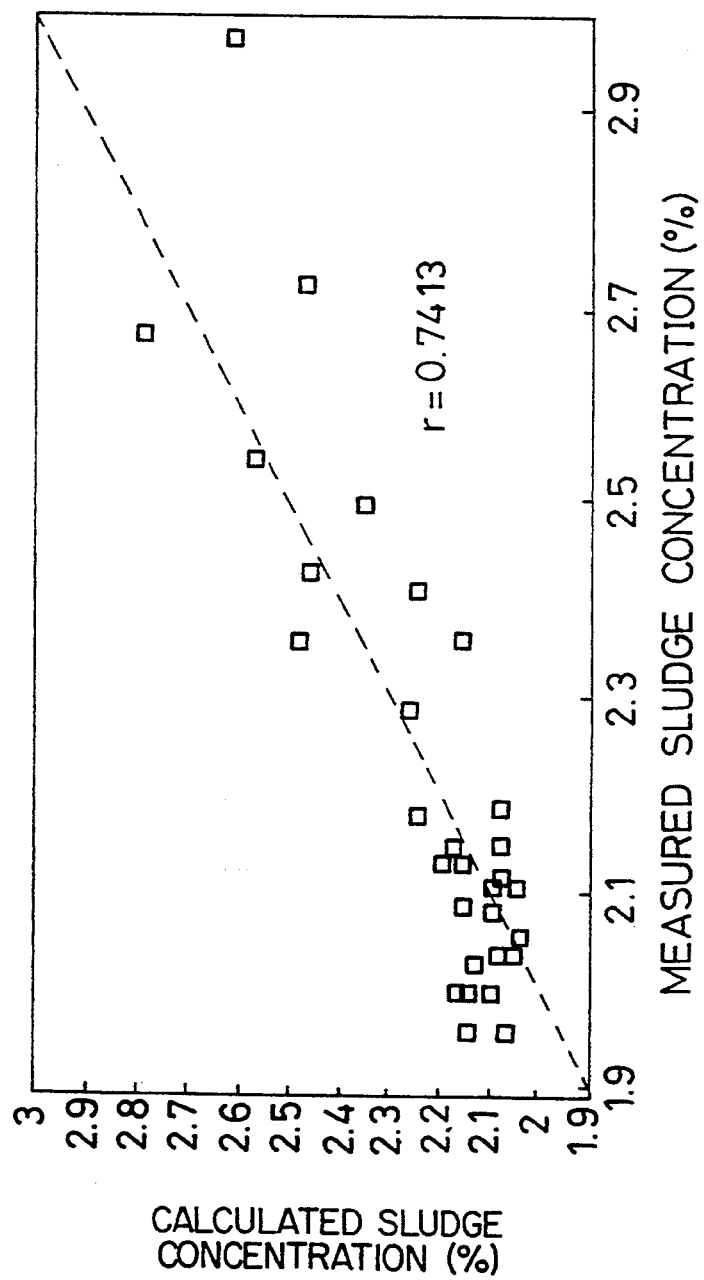

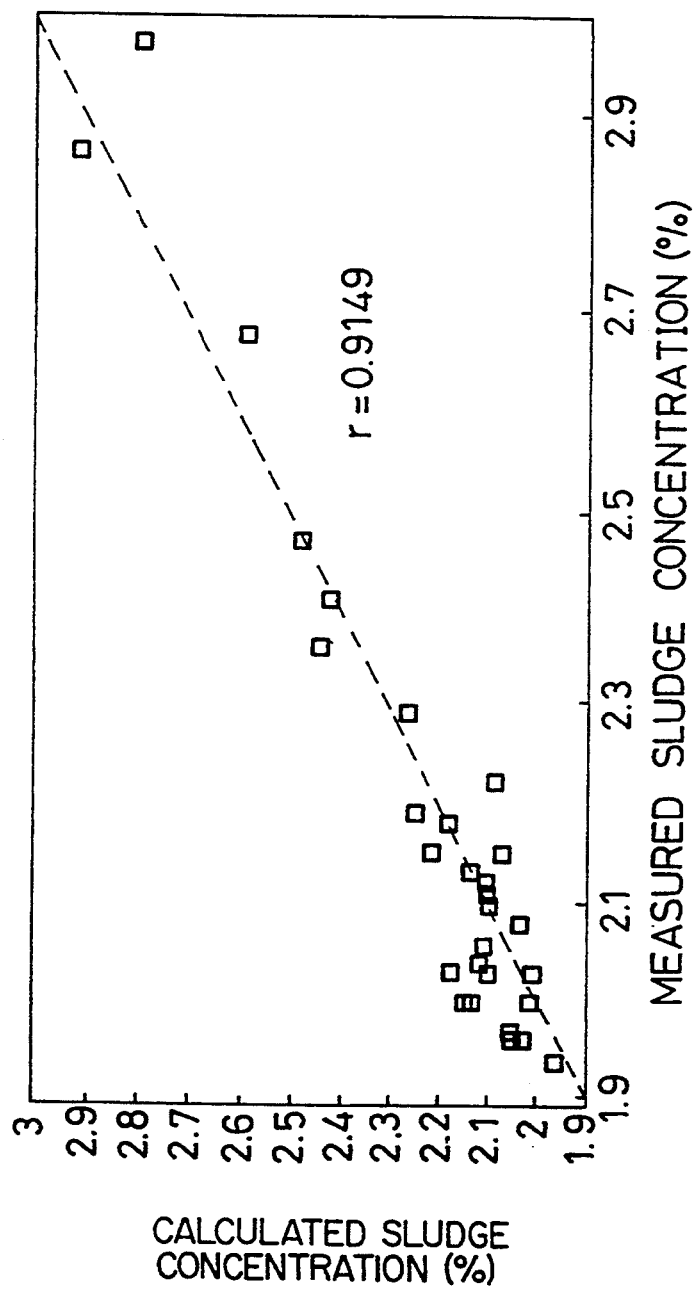

F I G. 15
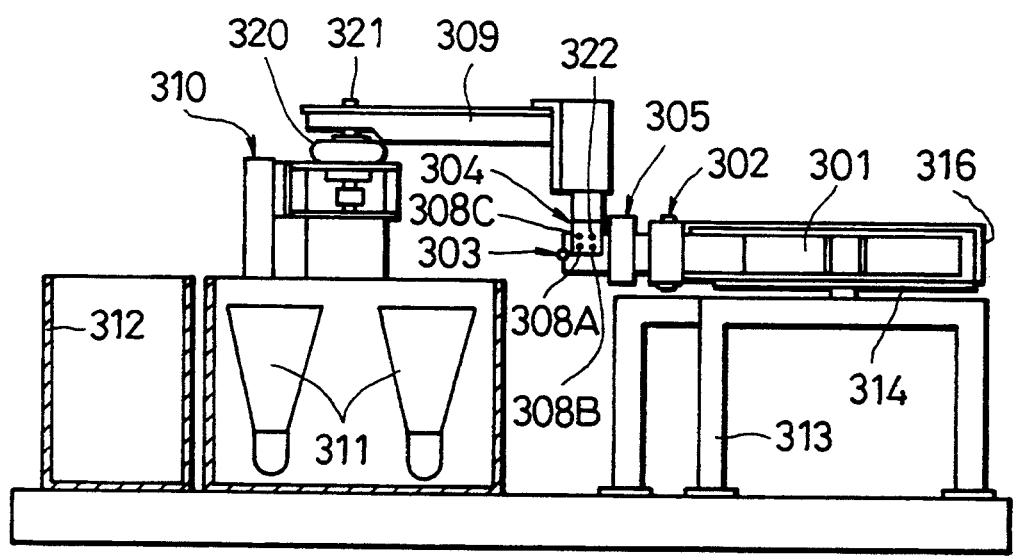

METHOD AND APPARATUS FOR CONTROLLING SLUDGE DEWATERING

BACKGROUND OF THE INVENTION

1. Field of the Invention

The present invention relates to a method for controlling the dewatering of sludge which comprises the step of adding an optimum amount of an organic polyelectrolyte coagulant to sludge produced in facilitier for the treatment of sewage, human excreta or industrial waste water and the like to efficiently dewater the sludge, and it also relates to an apparatus for controlling the dewatering of sludge.

2. Description of the Prior Art

In general, for example, in a dewatering process for sludge produced in a sewage treatment plant, an organic polyelectrolyte coagulant (hereinafter referred to as "polyelectrolyte coagulant" or simply "coagulant") is added to the sludge, and then dewatered cake is formed by a dewatering device. Conventional techniques for adding the coagulant are described in Japanese Patent Publication No. 31932/1982 and Japanese Patent Application Laid-open No. 25598/1985.

In a method for adding the coagulant which is described in Japanese Patent Publication No. 31932/1982, the concentration of the raw sludge is first measured, and the quantity of the sludge to be fed to a dewatering device and the amount of the coagulant to be added are then controlled on the basis of the measured concentration of the raw sludge.

In another method for adding the coagulant which is described in Japanese Patent Application Laid-open No. 25598/1985, the capillary suction time (hereinafter referred to simply as "CST"), defined below, of the coagulant-treated sludge containing the added coagulant is first measured, and an optimum coagulant dosage level at which the CST is minimized is determined based on the relation between the amount of the coagulant added and the CST of the coagulant-treated sludge. The actual coagulant dosage level is decided by multiplying the optimum coagulant dosage level by a factor.

CST is defined as the length of time required for a liquid to be absorbed by a fixed area of capillary material via capillary suction.

In the above-mentioned former method for measuring the concentration of the raw sludge, the raw slurry is introduced into the coagulant addition step via a thickening tank, and therefore the concentration of the sludge changes with the passage of the time, so that the necessary amount of the coagulant to be added varies. However, since the amount of the coagulant has been already determined on the basis of the concentration of the raw sludge, the amount of the coagulant cannot be properly controlled at times.

On the other hand, in the latter method for deciding the amount of the coagulant by measuring the CST of the coagulant-treated sludge, the CST tends to decrease with the increase of the coagulant amount, but it increases when the amount of the coagulant is in excess of a certain level. The CST being low means that sludge has grown to larger flocs. Therefore, if the amount of the coagulant is adjusted so that the CST may be minimized, it is sure that the sludge can be efficiently dewatered.

In this method, the CST is measured in the sludge containing the added coagulant, but it is very difficult to collect small representative samples of the coagulant-treated sludge due to the uneven distribution of flocs in said sludge. Thus, the flock amount is different each time the coagulated sludge is sampled, so that the measured values of the CST fluctuate and thus are unreliable, with the result that it is hard to properly control the amount of the coagulant.

In accordance with this method, a test was made in a sewage treatment plant by the present inventors. In this test, the estimated proper amount of the coagulant was added to a raw sludge (where the CST would be minimized) and the excessive amount of the coagulant was added to the raw sludge (where the CST would fairly increase). Afterward, each coagulant-treated sludge was sampled several times, and the CST (seconds) was then measured. As a result, with regard to the samples containing the proper amount of the coagulant, the measured CST values, for example, were 7.6, 9.9, 7.8, 9.7 and 8.3 seconds, and with regard to the samples containing the excessive amount of the coagulant, the measured CST values, for example, were 21.2, 13.0, 13.6, 19.7 and 19.8 seconds.

In both the cases, the measured CST values fluctuated greatly.

Incidentally, the above-mentioned measurement of the CST was made by the use of the undermentioned measuring device.

In addition to the above-mentioned methods, there have been suggested a dewatering control method utilizing a colloid charge amount (Japanese Patent Application Laid-open No. 200899/1986) and another control method utilizing an anion degree (Japanese Patent Application Laid-open No. 132599/1987). In the dewatering control method utilizing the colloid charge amount, the colloid charge amount of the sludge is first measured, and from the thus measured value, indications of the concentration and the characteristics of the sludge are determined. On the basis of these indications, conditions such as the sludge feed flow rate, the coagulant dosage level, the stirring strength of a mixing tank, the dewatering time and dewatering pressure are most properly controlled. In the control method utilizing the anion degree, the amount of crude suspended solids in the sludge, the anion degree of the sludge, and the cation degree of the coagulant are measured, and the dosage level of the coagulant is shown as a linear function of these factors to determine an optimum coagulant dosage level.

However, in order to measure various factors such as the colloid charge amount of the sludge, the amount of the crude suspended solids, the anion degree of the sludge and the cation degree of the coagulant, expert knowledge of physics and chemistry and experience are required, and measuring these factors is complex and time-consuming. For example, in the case where sludge from primary settling tanks, a excess activated sludge, and digested sludge are mixed and treated in a sewage treatment plant, the mixing ratio of these sludges changes continually. Therefore, if the dosage level of the coagulant is controlled in accordance with these factors determined for a sample sludge which does not necessarily represent the actual sludge, no good control can be exercised and so it is very difficult to steadily and efficiently dewater the sludge in the real sewage treatment plant.

SUMMARY OF THE INVENTION

An object of the present invention is to provide a method and an apparatus for controlling the dewatering of sludge by which the above-mentioned problems can be solved and which permits properly adding a coagulant to the sludge to reduce the water content in a dewatered cake.

A first method for the dewatering control of sludge which can achieve the above-mentioned object of the present invention is a control method for improving the dewatering efficiency of the sludge by successively adjusting the addition of a polyelectrolyte coagulant in a process where the polyelectrolyte coagulant is added to the sludge to coagulate the solids in the sludge, followed by its dewatering to separate the sludge into dewatered cake and filtrate, the aforesaid method being characterized in that the CST of the filtrate is successively measured, and the addition of the polyelectrolyte coagulant is accordingly adjusted so that the capillary suction time of the filtrate may be minimized.

A second method for controlling the dewatering of sludge control of the present invention is a control method for improving the efficiency of sludge dewatering which comprises successively adjusting the addition of a polyelectrolyte coagulant in a process where the polyelectrolyte coagulant is added to the sludge to coagulate the solids in the sludge, followed by its dewatering to separate the sludge into cake and filtrate, the aforesaid method being characterized in that the CST of the sludge and the CST of the filtrate are successively measured, and the addition of the polyelectrolyte coagulant is accordingly adjusted so that the decrease ratio of CST, defined below, may be maximized:

*decrease ratio (%) of capillary suction time*
$(CST) = (the\ CST\ of\ the\ sludge - the\ CST\ of\ the\ filtrate)/(the\ CST\ of\ the\ sludge) \times 100$ Furthermore, the present invention is directed to apparatus for controlling the dewatering of sludge by which the above-mentioned control methods can be carried out.

In a sludge dewatering system having a coagulant addition means for adding a polyelectrolyte coagulant to sludge and a dewatering means for dewatering the sludge which has been subjected to coagulation reactions by the addition of the coagulant, a first apparatus for controlling the dewatering of sludge comprises a measuring means for successively measuring the CST of the filtrate discharged from the dewatering means, and a control means for controlling the coagulant addition means based on the filtrate CST to control the addition of the coagulant.

In the sludge dewatering system, a second apparatus for controlling the dewatering of the sludge comprises a measuring means for successively measuring the CST of the sludge, a measuring means for successively measuring the CST of the filtrate discharged from the dewatering means, and a control means for controlling the coagulant addition means based on the decrease ratio which is defined above, calculated by the control means to control the addition of the coagulant. The above-mentioned method for controlling the dewatering of the sludge according to the present invention has been contrived based on the finding that if the dosage ratio of the coagulant, defined below, is the most appropriate, the CST of the filtrate is always minimized:

*dosage ratio (%) = amount of coagulant/solid content of sludge × 100*

The phase "The most appropriate dosage ratio" can be defined as the dosage ratio at which the coagulant does not remain as such (nonreacted) due to too high a dosage ratio or the solids in the sludge do not remain as such (uncoagulated) due to too low a dosage ratio so that it is possible to separate the sludge into cake having a low water content and filtrate. However, it is very difficult to successively determine the most appropriate dosage ratio because the most appropriate dosage ratio varies with the characteristics of the sludge and especially, the value of the solids content of sludge itself, used to calculate the ratio using the above calculation formula, fluctuates. According to the present invention, the control of the dewatering of sludge at the most appropriate dosage ratio of the coagulant can be achieved by successively measuring the CST of the filtrate and accordingly adjusting the addition of the coagulant in order to minimize the capillary suction time, whereby improvements in the efficiency of sludge dewatering can be realized to a great extent.

Furthermore, if the CST relative data of the filtrate and the sludge are employed, the sludge dewatering control can be accomplished with higher precision.

The filtrate produced by sludge dewatering sometimes contains some fine particles which are not captured by the usual dewatering means, but even if it contains them, a stable measurement of its CST is still possible, because there is little fluctuation in the characteristics of the filtrate samples collected under the same conditions and therefore little fluctuation in the CST's determined for such filtrate samples. A minimum CST value of the filtrate corresponds to the optimum dosage ratio of the coagulant, and therefore the amount of the coagulant can be extremely precisely added to the sludge, whereby the sludge can be dewatered so effectively that the dewatered cake has a low water content.

In addition, the above-mentioned apparatus for the control of the dewatering of the sludge according to the present invention is simply constituted so as to measure the CST of the filtrate, whereby the control of the dewatering of sludge can be achieved with high precision.

BRIEF DESCRIPTION OF THE DRAWINGS

FIG. 4 shows a block diagram of a concentration measuring device (1).

FIG. 5 shows a block diagram of a concentration measuring device (2).

FIG. 6 shows a block diagram of a concentration measuring device (3).

FIG. 7 shows a block diagram of a concentration measuring device (4).

FIG. 8 shows the relation between the calculated sludge concentration and the measured sludge concentration.

FIG. 9 shows another relation between the calculated sludge concentration and the measured sludge concentration.

FIG. 15 shows a schematic front view of the apparatus shown in FIG. 14.

DETAILED DESCRIPTION AND THE PREFERRED EMBODIMENTS

In the present invention, sludge to be treated include those produced in facilities for the treatment of sludge, human excreta, industrial waster water and so forth, and no particular limitations exist in the type of sludge.

In the present invention, many known polyelectrolyte coagulants can be used. Examples of the coagulant include polyaminoalkylmethacrylates, polyaminoalkylmethacrylates and their copolymer, polyacrylamide mannich modified product, polyacrylesteracrylamide copolymer, polyamines, polyethyleneimine, dicyandiamine, chitosan, polyacrylamide, polyethylene oxide, sodium polyacrylate, acrylamide-sodium acrylate copolymer, polyacrylamide partial hydroysis product, carboxylmethyl cellulose, and the like, and the suitable coagulant can be selected therefrom depending upon the characteristics of the sludge to be treated.

Figure 1:
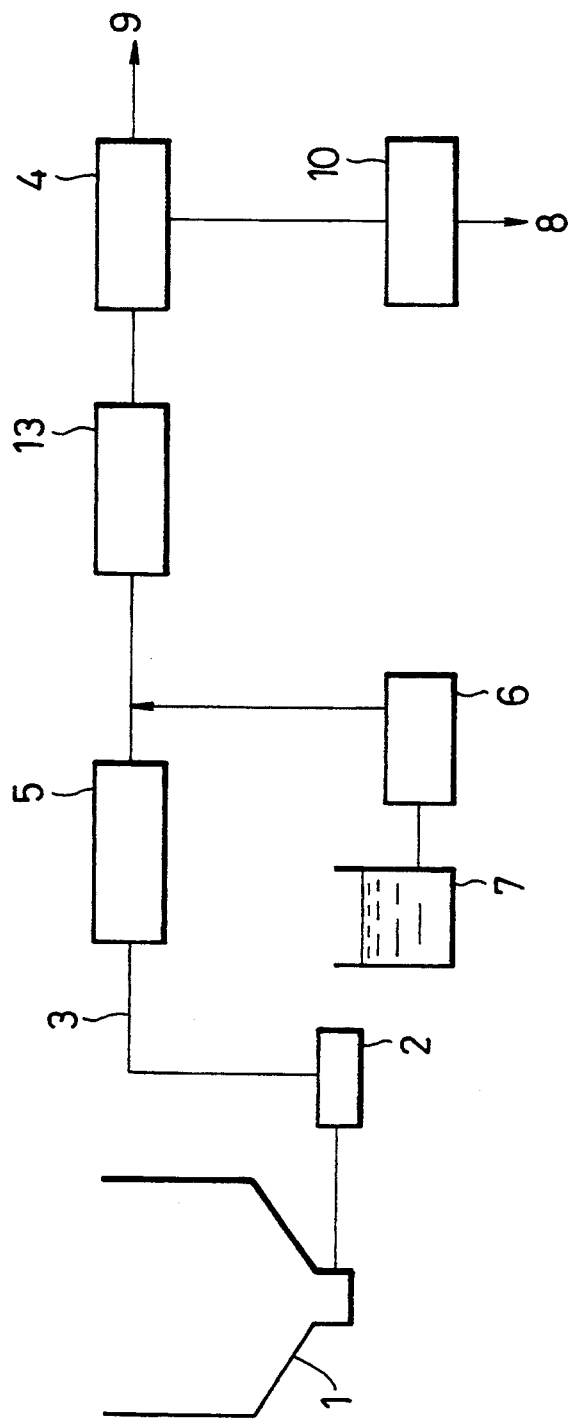
FIG. 1 shows a block diagram illustrating one embodiment of an apparatus for the control of the dewatering of sludge according to the present invention.

FIG. 1 shows a block diagram illustrating one embodiment of a sludge dewatering control apparatus which can effectively carry out the method for controlling the dewatering of the sludge according to the present invention.

Reference numeral 1 is a sludge tank, and the sludge is fed to a dewatering means (4) through a sludge feed pipe (3) by a sludge pump (2) constructed, for example, so as to automatically adjust the flow rate of the sludge by remote control. Examples of the dewatering means (4) include a vacuum filter, a filter press, a centrifugal separator, a belt press type filter and a screw press. Numeral 5 is a sludge concentration (SC) measuring means for measuring the sludge concentration in the sludge feed pipe (3), and this SC measuring means will be hereinafter described in detail. Incidentally, the SC measuring means (5) is provided only where required and may otherwise be omitted.

Reference numeral 6 is a coagulant pump for feeding a known organic polyelectrolyte coagulant stored in a coagulant tank (7) to the slurry feed pipe (3), and the point of dosing the coagulant is on the downstream side of the SC measuring means (5), so that the concentration of the raw sludge can be measured by the SC measuring means (5). The sludge to which the coagulant has been added is then introduced into a coagulant reaction device (13), in which the sludge is coagulated and sludge flocs are formed. In some cases, the coagulant reaction device (13) can be omitted, depending upon the type of the dewatering means (4). For example, when a centrifugal separator or the like, in which the difference in the revolving speed between a screw and a bowl exerts a sharing force, thereby promoting the coagulation reaction, is used as the dewatering means, the coagulant reaction device (13) can be omitted.

The coagulant reaction device (13) promotes the coagulation reaction between the coagulant and the solids in the sludge, and typical examples of the coagulant reaction device (13) include a dynamic type such as a horizontal drum mixer, a vertical agitator and the like, and a static type such as a line mixer and the like. Reaction conditions (temperature, time, stirring degree and the like) can be suitably selected depending upon the kinds of coagulant and sludge, and the like.

When fed to the dewatering means (4), the sludge containing the flocs is separated into filtrate (8) and dewatered cake (9). A filtrate CST measuring means (10) measures the CSTs of the filtrate coming from the dewatering means (4). The filtrate (8) at times contains fine particles which have not been captured by the dewatering means (4), but there is little fluctuation in the CTSs determined for different samples so long as the same source sludge is being dewatered so there is no problem. The measurement principle of the CST is known, and therefore any detailed description is here omitted. In the present embodiment, the CSTs are automatically measured by a device shown in FIG. 2.

Figure 2:
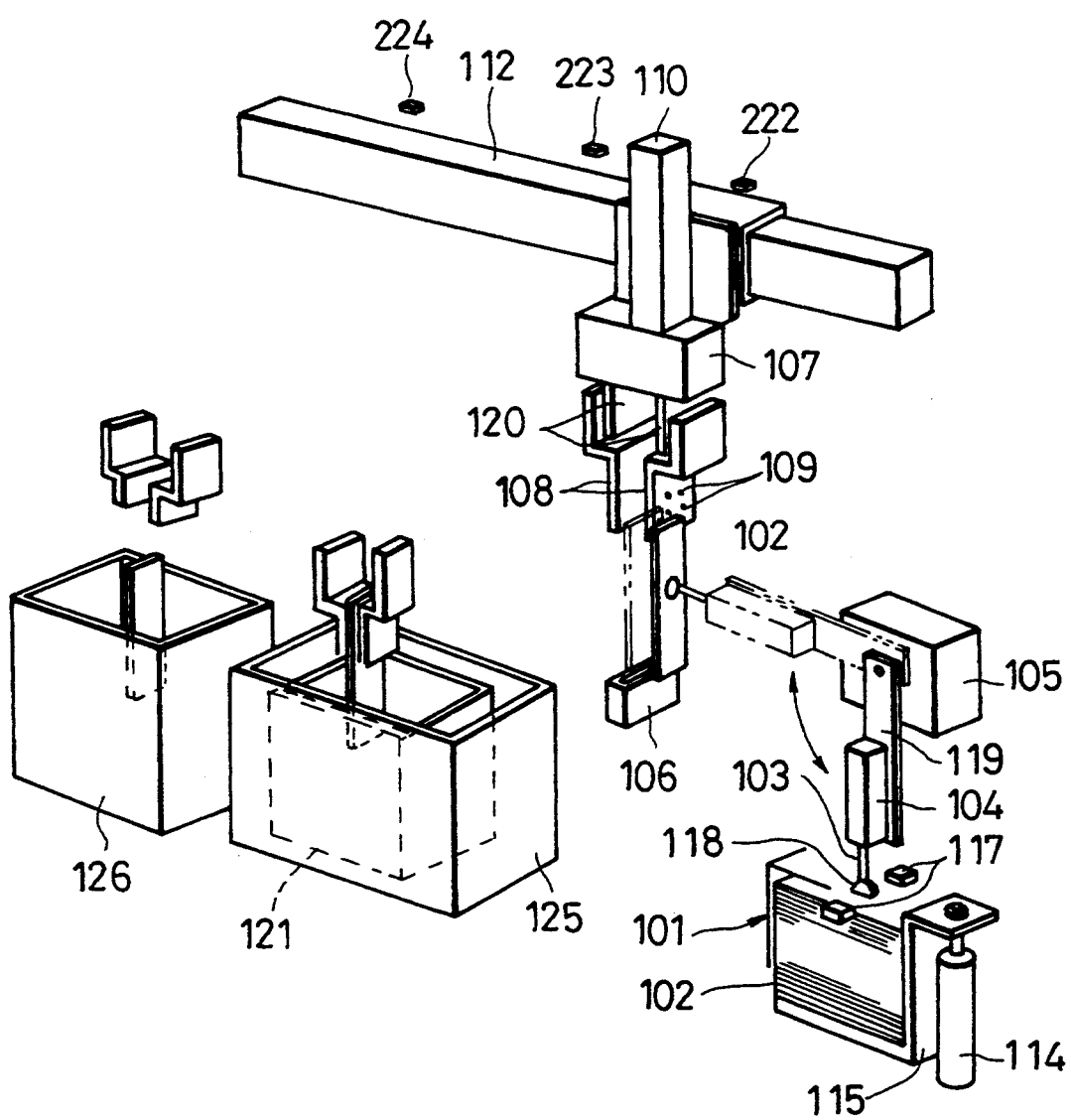
FIG. 2 shows a schematic perspective view of a filtrate CST measuring device.

The device shown in FIG. 2 has an inlet pipe (not shown) and an outlet pipe (not shown) of the filtrate (8). In this device, a filter paper (102) held by a pair of filter paper holding plates (108) is immersed to a predetermined position in a filtrate pot (121) (whose periphery is covered with an outer container (125) so as to prevent the filtrate from flying about) in which the filtrate (8) is automatically stored by an automatically openable and closable valve (not shown), and a time until the filtrate (8) rises along the filter paper (102) to a pair of electrodes (109) disposed on the pair of filter paper holding plates (108) by a capillary suction phenomenon is then measured by a time meter (not shown). The time thus measured is CST (seconds). After the measurement, the used filter paper is thrown into an adjacent filter paper disposal pot (126). Many filter papers (102) are heaped on a heap plate (115) of the filter paper holder (101), and an air cylinder (114) drives until a photosensor (117) detects that the uppermost filter paper reaches a predetermined position. The parallelly disposed uppermost filter paper (102) is delivered in a vertical state to a filter paper receiver (106) by a suction type delivery mechanism and then held by the pair of filter paper holding plates (108).

This suction type delivery mechanism comprises an actuator (105) which can rotate 90°, an arm (119) which can be rotated by the actuator (105), an air cylinder (104) attached to the arm (119), a cylinder rod (103) extending from the air cylinder (104), and a suction member (118) attached to the tip of the cylinder rod (103). The filter paper (102) is sucked and held by this suction member (118) (when a film is laminated on the back surface of the filter paper, a high airtightness is given, so that suction state is keep good), and it is then rotated 90° and conveyed to the paper receiver (106).

The pair of filter paper holding plates (108) are attached to a pair of air chuck plates (120), respectively, and the filter paper (102) is held by feeding air toward an actuator (107). Furthermore, the pair of filter paper holding plates (108) are caused to rise and fall by driving a rising/falling air cylinder (110). This rising/falling air cylinder (110) can be moved along a parallel slide axis (112) comprising a rodless air cylinder and the like so as to automatically stop at a filter paper holding position, a measuring position and a filter paper disposal position by limit switches (222), (223) and (224), respectively. The CSTs of the filtrate are successively measured at an interval of a certain time, and the measured results are forwarded to a control means (not shown), by which the amount of the coagulant to be fed by the coagulant pump (6) is controlled.

The CST values vary with the kind of capillary medium and a measurement manner of the capillary absorption times. However, the CST values are relatively evaluated, and so their absolute values are not influential. For this reason, it is not important what kind of capillary medium and what measurement manner are employed, so long as the same capillary medium and the same measurement manner are used.

The CST values of the filtrate were actually automatically measured under the same conditions as in the conventional example described under the heading "Description of the Prior Art". In the case where the coagulant was added in a proper amount, the measured CST data, for example, were [7.2, 7.8, 8.1, 7.6 and 7.4 seconds], and in the case where the coagulant was added in an excessive amount, the measured CST data, for example, were [16.6, 16.2, 15.1, 15.1 and 15.7 seconds].

These data are much more stable as compared with the conventional example wherein the CST of slurry upon the addition of coagulant were measured. In consequence, it can be understood that when the CSTs of the filtrate are measured, there is little fluctuation in the data and the measured values are more reliable.

In the above example, filter paper No. 585 (approximate thickness is 1 mm) used for chromatography produced by ADVANTEC TOYO was used as the capillary material. In addition to said filter paper, filter paper No. 526 of the same company, filter paper Chr #3 produced by WATTMAN and the like can be used without particular limitations. The distance between the pair of electrodes (109) was set at 10 mm.

The addition of the coagulant can be optimized simply by determining the CST values of the filtrate because the CST of the filtrate is steady and reliable as an index to control the dewatering system, and a coagulant dosage level which gives the minimum CST of the filtrate is the optimum one. In this regard, the CST value is important as a relative value, meaning that it is necessary to compare the CST values to each other to control the addition of the coagulant. However, it is not possible to objectively define the conditions of a sludge dewatering system by using the CST value of filtrate alone because the coagulant dosage ratio cannot be calculated from the filtrate CST value. In order to objectively define the sludge dewatering system, the coagulant dosage ratio should be employed in place of the amount of the coagulant, although it is possible to control the system sufficiently only by adjusting the amount of the coagulant. Thus, in the actual operation, the CST of the filtrate is successively measured and, accordingly, the addition of the coagulant is adjusted so that the coagulant is added at an optimum dosage ratio dictated by the shortest CST value. The dosage ratio of the coagulant is defined as follows:

$$\text{Dosage Ratio (\%)} = \text{the amount of the coagulant}/\text{the solid content of the sludge} \times 100$$

Specifically, the addition ratio is further defined as follows:

$$\text{Dosage Ratio (\%)} = (\text{coagulant solution flow} \times \text{coagulant concentration}) \div (\text{sludge feed flow} \times \text{sludge concentration}) \times 100$$

In FIG. 1, the optimum dosage ratio as well as amount of the coagulant can be determined as follows: The flow of the coagulant solution is increased and decreased on the basis of the SC information, the sludge feed flow input by the SC measuring means (5) as well as a coagulant solution flow input by the coagulant pump (6) and the concentration of coagulant solution, and, correspondingly, the CST values of the respective filtrates are compared with each other to determine the coagulant dosage level (ratio) which permits minimizing the CST value. As the SC measuring means (5) for detecting the concentration of the sludge in FIG. 1, these are known means based on a weight method, a defoaming method, a dielectric constant method, etc. In addition to these, the SC measuring means described hereinafter can also be used.

The coagulant dosage ratio is also referred to as the coagulant dosage ratio to TS in sludge. TS means the total solids content and clarifies the definition of the coagulant dosage ratio which is not based on the weight of sludge but on TS in sludge. Hereinafter, the coagulant dosage ratio always means the coagulant dosage ratio to TS in sludge.

If the various values determined as mentioned above are memorized by a memory means (not shown in FIG. 1), they can be used for the subsequent control.

Figure 3A:
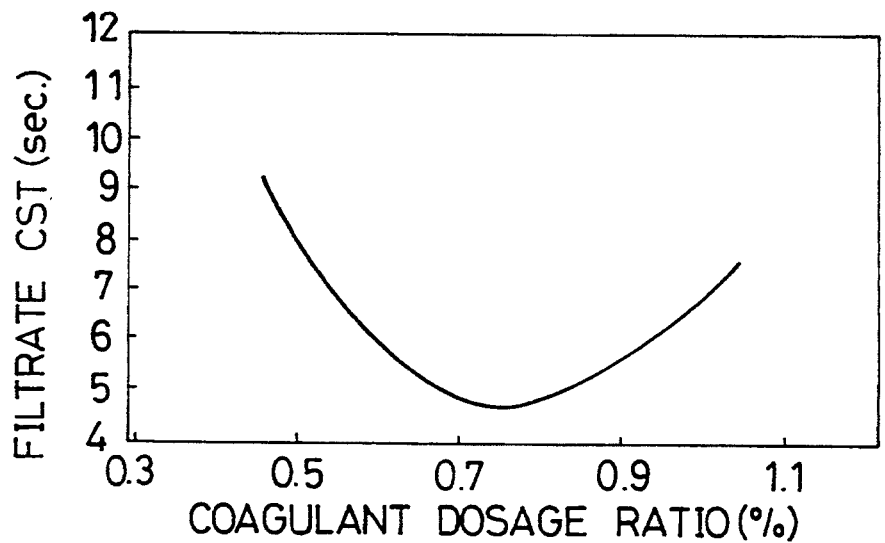
FIG. 3 shows the relation (A) between the CST of filtrate and the coagulant dosage ratio, and the relation (B) between the cake moisture content and the coagulant dosage ratio.
Figure 3B:
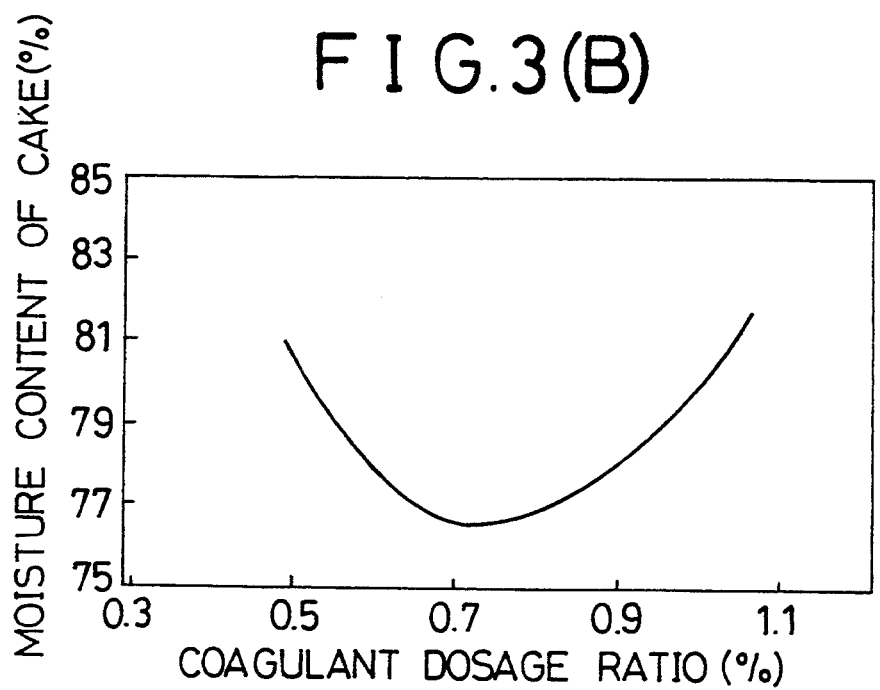

FIG. 3, for example, shows the relation between the CSTs of the filtrate and the coagulant dosage ratio which was obtained on the basis of the memorized data, and the relation between the coagulant dosage ratio and the moisture content in the cake. FIG. 3 is based on the data obtained from dewatering tests conducted on the sludge produced in a certain sewage treatment plant under the following conditions:

Sludge to be dewatered: raw mixed sludge produced in a sewage treatment plant
Sludge concentration (TS): 2.6–3.4 w/w % (weight method)
Coagulant: polyaminoalkylmethacrylate
Coagulant concentration: 0.3%
Dewatering equipment: a belt press filter
Sludge feed flow: 17–23 m³/H
Coagulant solution flow: 0.8–1.5 m³/H In FIG. 3(A) showing the relation between the CSTs of the filtrate and the coagulant dosage ratio, the CSTs of the filtrate are minimized in the vicinity of a coagulant dosage ratio of 0.75%. Furthermore, in FIG. 3(B) showing the relation between the coagulant dosage ratio and the moisture content of the cake, the moisture content of the cake is similarly minimized in the vicinity of a coagulant dosage ratio of 0.75%.

Therefore, it is apparent that the coagulant dosage ratio which gives the minimum filtrate CST is approximately the coagulant dosage ratio which gives the minimum moisture content of the cake, and the shapes of the two curves are very similar to each other.

The coagulant dosage ratio at which the CST of the filtrate was minimized was 0.75% in the above-mentioned embodiment, but this optimum dosage ratio varies with the type of the dewatering device, the amount of the sludge to be dewatered, the kind of coagulant, and so forth. In the present invention, the fact that there is an optimum dosage ratio which permits minimizing the CST of the filtrate is important. In addition, it is also important that the coagulant dosage ratio which makes the CST of the filtrate minimum is also the coagulant dosage ratio which makes the moisture content of the cake minimum. In other words, the moisture content of the cake can be controlled with high precision by utilizing the CST of the filtrate as an index.

Next, reference to a control operation of the present embodiment will be made. In the first place, a suitable amount of the coagulant is added to the fed slurry, and dewatering is then started by the dewatering means (4). CSTs of the filtrate (8) discharged from the dewatering means (4) are measured by the filtrate CST measuring means (10), and the CST values thus measured are then memorized by the above-mentioned memory means.

Next, the amount of the coagulant is slightly increased, and after the passage of a predetermined time, the CST values of the filtrate are similarly measured again. In the case where the later CST values are larger than the previous CST values, it can be judged that the coagulant added is in excess of the optimum dosage ratio, because the CST values of the filtrate increase though the amount of the coagulant is increased. Therefore, in such a case, the amount of the coagulant is to be decreased.

On the other hand, when the later CST values of the filtrate containing the decreased amount of the coagulant are larger than the previous CST values of the filtrate, it is meant that the CST values of the filtrate increase owing to the decrease of the coagulant amount. Therefore, it can be judged that the amount of the coagulant is short, and the amount (dosage ratio) of the coagulant is to be increased. In this way, the CST values are measured at regular intervals, and the amount of the coagulant is controlled so that the CST values may be minimized, whereby the coagulant can be added in an optimum dosage ratio.

When the dosing of the coagulant begins with an optional dosage level, a long period of time is taken before the optimum dosage level has been reached, and the efficiency of the dewatering treatment is also poor during such a preparatory operation. If the approximate optimum amount of the coagulant to be added to the sludge is determined beforehand based on the characteristics of the sludge to be treated, the kind of coagulant and the like by a coagulation test or the like, the optimum control of the sludge dewatering can be achieved in a short period of time.

Figure 16:
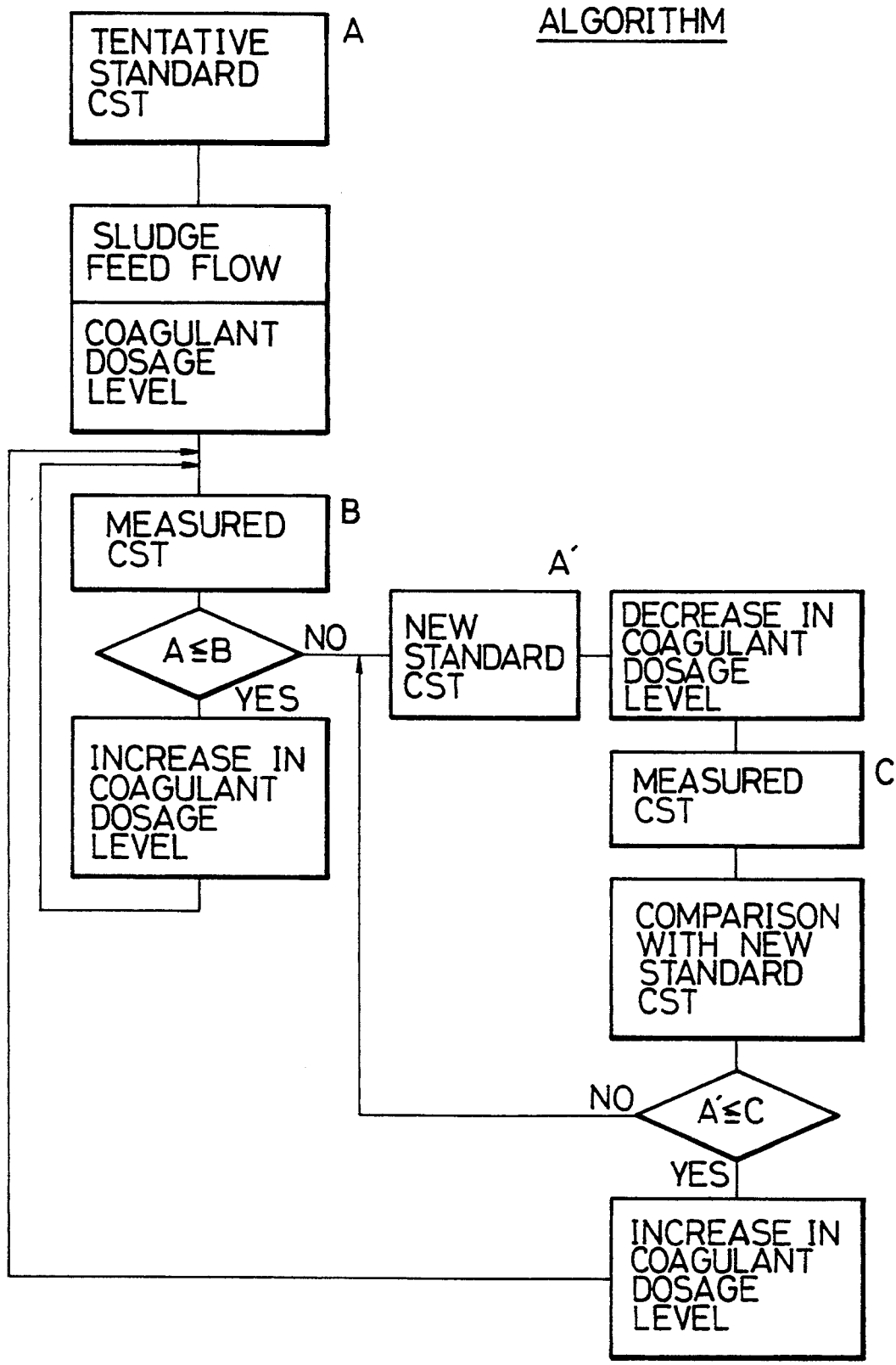
FIG. 16 shows an algorithm indicating the control flow of the first sludge dewatering system according to the present invention.

FIG. 16 shows an algorithm indicating the control flow of a sludge dewatering system. First, a tentative standard CST(A) is set and operation starts (the tentative standard CST is normally set to a little higher level than the supposed minimum CST and the dosage level of the coagulant is normally set at a little less than the supposed optimum CST.). After a certain period of time (i.e., at least after the amount of time required until the sludge containing the predetermined amount of the coagulant finally reaches a filtrate CST measuring point), the CST of the filtrate is measured (B) and compared with the tentative standard CST(A). If B is longer than A, the coagulant dosage level is considered to be insufficient and, accordingly, the dosage level of the coagulant is increased (by approximately 10%) and then the CST is measured again (B'). If B' is still longer than A, the dosage level is further increased until the successive measurement of B' (B'') becomes shorter than A. The fact that B'' is shorter than A means that a shorter CST than the tentative standard CST(A) exists. Therefore, the standard CST is changed to A' (i.e., B'') from A and the coagulant dosage level is decreased (by approximately 10%) in order to determine the minimum CST (i.e., the optimum dosage ratio). After the decrease in the dosage level, the CST is measured (C) and compared with the new standard CST (A'). If C is longer than A', the dosage level is considered to be insufficient and, accordingly, the dosage level is increased and continuously controlled in the same way as described above. If C is shorter than A', a smaller CST than A' exists, and thus the standard CST is changed to a shorter one and continuously controlled in the same way as described above. When the control of dosage level is exercised in accordance with the above-mentioned procedure, it is possible to pinpoint the optimum conditions only by using the CST value of the filtrate as an index. In general, the feedback system based on the change in the coagulant dosage level in response to the change in the CST of the filtrate functions well because the feedback is quicker than the change in the characteristics of sludge.

Although the foregoing explanation of the algorithm as shown in FIG. 16 is based on the coagulant dosage level, the control procedure can also be followed on the basis of the coagulant dosage ratio calculated from the dosage level.

The control of the dewatering of sludge according to the present invention is based on the knowledge that when the CST of the filtrate is minimized, the coagulant dosage ratio is the most appropriate. However, the control of the coagulant dosage level can also be exercised on the basis of a dosage ratio lower than the optimum one as a practical operation. More specifically, the relation between the moisture content of the dewatered cake and the dosage ratio of the coagulant is depicted by a nearly quadric curve, as shown in FIG. 3(B). As is apparent from this drawing, even if the dosage ratio of the coagulant slightly changes in the vicinity of the minimum value of the moisture content in the dewatered cake, the moisture content of the cake does not increase very much in this range.

Therefore, if it is desired to save the amount of the coagulant to the utmost, the dewatering means can be operated at a dosage ratio slightly smaller than the above-mentioned optimum dosage ratio in the range in which the moisture content of the cake does not increase very much even when the dosage ratio is reduced. In the above-mentioned range, the sludge dewatering means can be operated at dosage ratios obtained by multiplying, by a factor of about 0.7 to about 1.0, the dosage ratio of the coagulant which permits minimizing the CST of the filtrate. Strictly speaking, the quasi-quadric curve in FIG. 3(B) varies with the treatment conditions, but any curve can show a similar shape having the minimum value of cake moisture content. Therefore, even if the dosage ratio which gives the minimum moisture content of cake changes depending on the treatment conditions, it is always the case that the moisture content of the cake is substantially minimized at dosage ratios between about 0.7(70%) and about 1.0(100%) of the optimum dosage ratio.

The constitution of the present invention described above is based on the knowledge that the dosage ratio of the coagulant which makes the CST of the filtrate minimum permits minimizing the moisture content of the cake. As long as the dosage level is used as the control index, the instrumentation of the corresponding dosage ratio of the coagulant is not necessary. In order to convert the dosage level to the dosage ratio, it is necessary to determine the sludge concentration. Therefore, reference to a method for measuring the concentration of the sludge will be made.

As the SC measuring means (5) for detecting the concentration of the sludge in FIG. 1, there are various means based on a weigh method, a defoaming method, a dielectric method and so forth. In general, in dewatering facilities, the concentration of fed sludge varies with the time of day, the day of week, and the season. Therefore, if the dosage level of the organic polyelectrolyte coagulant is adjusted in accordance with the fluctuation of the sludge concentration, the most desirable moisture content of the dewatered cake can be obtained.

However, among the above-mentioned means for detecting the concentration of sludge, the weight method can measure the sludge concentration with precision but this method takes a relatively long period of time to detect the sludge concentration. On the other hand, there are fluctuations in the values detected by the defoaming method or the dielectric method, and therefore these methods are rather unsuitable for the instant detection of the sludge concentration. Thus, a concentration detecting means is preferred which can instantly detect the sludge concentration without much fluctuation.

As a concentration measuring device for measuring the sludge concentration which can meet the above-mentioned requirements, any one of the following devices can be utilized.

That is, as the factors which represent the characteristics of the sludge, there are temperature, viscosity, electrical conductivity, hydrogen ion concentration (pH), particle size distribution, anion degree, CST and the like, but the undermentioned measuring devices are constituted so as to calculate the sludge concentration from a suitable combination of the factors of the temperature, viscosity, electrical conductivity and CST of the sludge. The following four combinations are used in constituting these concentration measuring devices.

(1) The temperature of sludge and the CST of sludge.

(2) The temperature of sludge, the CST of sludge and the electrical conductivity of sludge.

(3) The temperature of sludge, the viscosity of sludge and the electrical conductivity of sludge.

(4) The temperature of sludge, the viscosity of sludge, the electrical conductivity of sludge and the CST of sludge.

In the sludge concentration measuring device based on the above-mentioned combination (1), as shown in FIG. 4, temperature data detected by a temperature measuring means (21) such as an alcohol thermometer, a mercury thermometer or an electrical thermometer and CST values measured by a CST measuring means (22) such as a device shown in FIG. 2 are input into converter A-1 of arithmetic device A, and a slurry concentration (SC) is then calculated by arithmetic unit A-2. The concentration thus calculated is then input into output unit A-3 to display it on a concentration display (not shown). Furthermore, for example, in order to control the initial dosage ratio of the coagulant and the like, the concentration information is input into output control unit A-4.

In the arithmetic unit A-2, a multivariate analysis (a regression analysis) is carried out, taking the sludge concentration (SC: %) as an object variate and taking the sludge temperature (T: °C.) and the CST (C: seconds) as interpretation variates, for example. As a result of the analysis, the obtained relation formula is programed, and when the interpretation variate is input, the sludge concentration is calculated in accordance with the relation formula and then output as a signal. To set up the program, any of the following three ways, for example, can be employed although the second method 2 permits more precise automatic control.

1 The relation formula is formulated on the basis of past data and is fixed.

2 The relation formula is automatically adjusted by continuously accumulating new data.

3 Periodically the relation formula is manually adjusted using new data.

One example of the relation formula (the regression formula) can be shown as follows. According to a research made by the present inventors, with regard to the sludge in the certain sewage treatment plant (which is the same as mentioned above), the following formula, for example, was obtained:

$$SC = -2.02 \times 10^{-2} \cdot T + 1.34 \times 10^{-2} \cdot C + 2.08 \quad \text{(Formula 1)}$$

The sludge concentration was determined by the weight method.

Therefore, if this formula is input into the arithmetic unit A-2 of the arithmetic device A shown in FIG. 4, the sludge concentration can be obtained at substantially real time on the basis of the temperature information and the CST information.

FIG. 8 shows the relation between the sludge concentration (the calculated value of the sludge concentration) calculated in accordance with the formula 1 and the sludge concentration (the measured value of the slurry concentration) measured by the known weight method, and the straight line shown by the dotted line in this drawing shows the correlation between two sets of differently determined sludge concentrations. The concentration measuring device used in this embodiment as shown in FIG. 4 could obtain the precise value substantially close to the corresponding value actually measured. The correlation factor r is 0.7413.

FIG. 5 shows a block diagram of the sludge concentration measuring device based on the combination (2) mentioned earlier, and this measuring device comprises the combination of the concentration measuring device shown in FIG. 4 and an electrical conductivity measuring means 23. The sludge concentration measuring device carries out a multivariate analysis, taking the sludge concentration as an object variate and taking the sludge temperature, the sludge CST and the electrical conductivity ($E_C$: μs/cm) as interpretation variates to obtain a formula, and calculates the sludge concentration in accordance with the obtained formula, as in the concentration measuring device based on the combination (1) mentioned earlier. The electrical conductivity $E_C$ of the sludge is measured by a known electrical conductivity meter, and this value is input into the arithmetic device A together with the sludge temperature information and the sludge CST. In the rithmetic device A, the regression formula obtained by the multivariate analysis is input, and the sludge concentration (SC) is calculated on the basis of the input information.

In this embodiment, the following formula 2, for example, was obtained by the multivariate analysis for the same slurry as used for formulating the above-mentioned formula 1.

$$SC = 2.02 \times 10^{-2} \cdot T - 1.40 \times 10^{-3} E_c + 1.14 \times 10^{-2} \cdot C + 5.81 \quad \text{(Formula 2)}$$

FIG. 9 shows sludge concentrations calculated by the sludge concentration measuring device in this embodiment vs. measured sludge concentrations, as in FIG. 8. The measurement precision as shown in FIG. 9 is higher than that shown in FIG. 8. A correlation factor r is 0.9149 in the case of FIG. 9.

The sludge concentration measuring device based on the combination (3) mentioned earlier, as shown in FIG. 6, utilizes a sludge viscosity (N: $C_p$) instead of the slurry CST information in the measuring device based on the combination (2) mentioned earlier, together with the slurry temperature and the slurry electrical conductivity as interpretation variates. In this sludge concentration measuring device as shown in FIG. 6, the sludge viscosity information detected by a viscometer means 24 such as a known coaxial double cylinder rotary viscometer is input into the arithmetic device A together with the sludge temperature information and the electrical conductivity information.

A regression formula used for the input into the arithmetic device A is the following formula 3, for example, obtained by a multivariate analysis in this embodiment for the same sludge as used for formulating the formula 1:

$$SC = 2.25 \times 10^{-2} \cdot T + 9.36 \times 10^{-3} N - 4.50 \times 10^{-4} \cdot E_c + 1.89 \quad \text{(Formula 3)}$$

Figure 10:
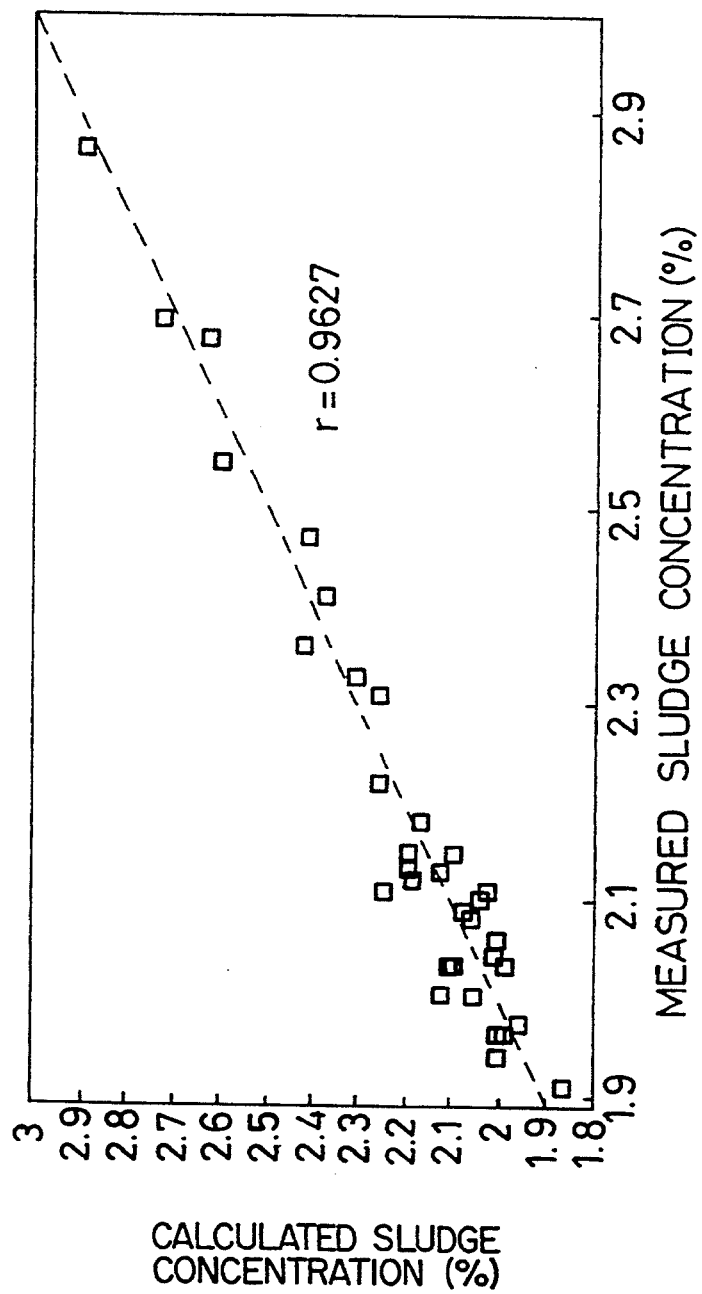
FIG. 10 shows still another relation between the calculated sludge concentration and the measured sludge concentration.

FIG. 10 shows sludge concentration values calculated by the slurry concentration measuring device in this embodiment vs. measured sludge concentration values, as in FIG. 8. The measurement precision as shown in FIG. 10 is higher on the side of high sludge concentrations than shown in FIG. 9. A correlation factor r is 0.9627 in the case of FIG. 10.

The slurry concentration measuring device based on the combination (4) mentioned earlier, as shown in FIG. 7, carries out a multivariate analysis, taking slurry temperature, viscosity, electrical conductivity and CST information as interpretation variates to obtain a regression formula, and inputs the obtained formula into the arithmetic unit A-2 in the arithmetic device A, whereby a slurry concentration is detected on the basis of these four sludge factors.

A regression formula used for the input into the arithmetic device A is the following formula 4, for example, obtained by the multivariate analysis in this embodiment for the same sludge as used for formulating the formula 1:

$$SC = 2.68 \times 10^{-2} \cdot T + 8.47 \times 10^{-3} N - 5.07 \times 10^{-4} E_C - 7.49 \times 10^{-3} \cdot C + 1.86 \quad \text{(Formula 4)}$$

Figure 11:
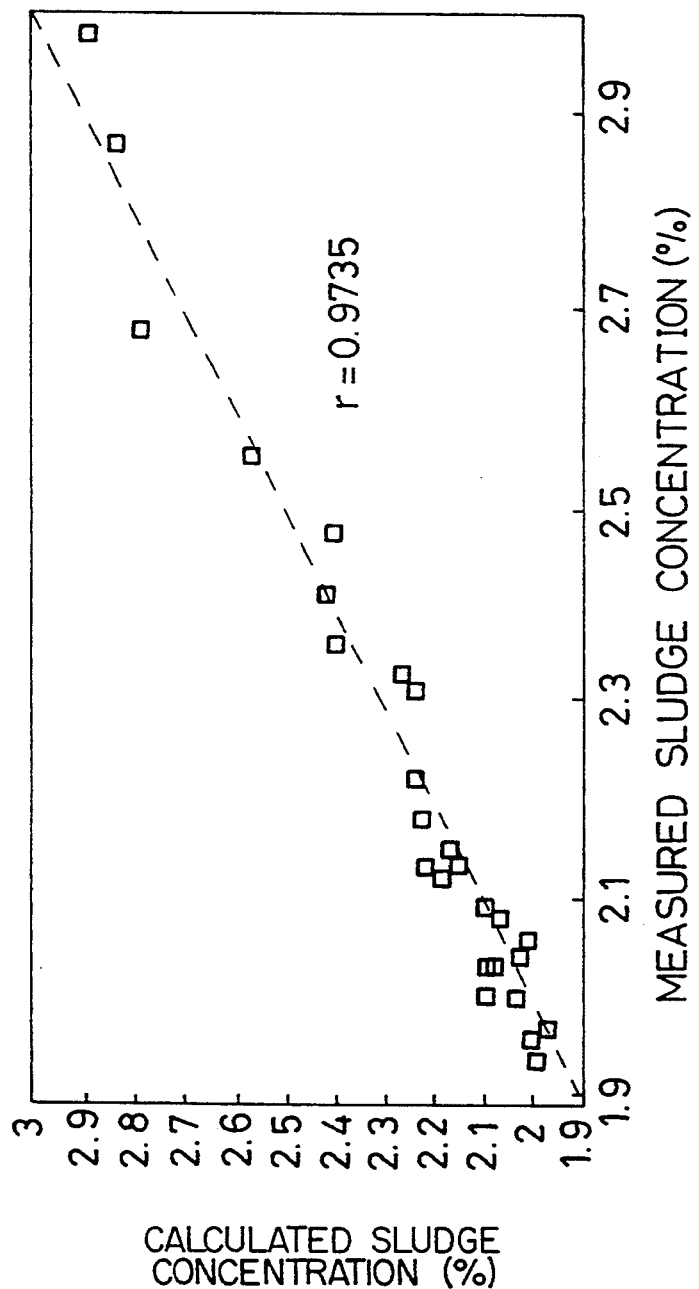
FIG. 11 shows the further relation between the calculated sludge concentration and the measured sludge concentration.

In this embodiment, the sludge concentration values collated closely with corresponding measured values in the whole range of low concentrations to high concentrations as compared with the other three embodiments mentioned above, as shown in FIG. 11. A correlation factor r is 0.9735 in the case of FIG. 11.

The principle of the control technique described above is that the dosage level (or the dosage ratio) of the coagulant to sludge can be controlled basically by utilizing the CST value of filtrate alone as an index. However, in accordance with the second method of the present invention, the dosage level of the coagulant can also be most properly controlled with even higher accuracy than the aforesaid first method, by utilizing both the CST value of the sludge itself before the addition of the coagulant and the CST value of the dewatering filtrate.

The second control method of the present invention is described hereinafter.

Figure 12:
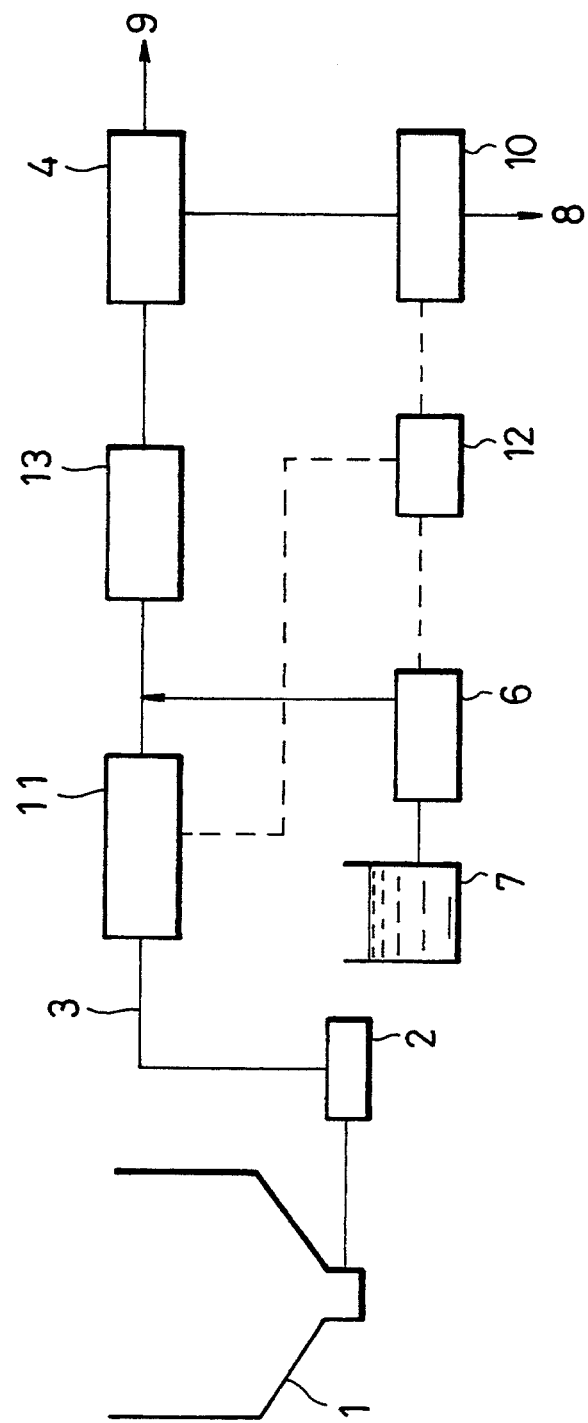
FIG. 12 shows a block diagram illustrating another embodiment of the apparatus for the control of the dewatering of sludge according to the present invention.

FIG. 12 shows one embodiment of an apparatus for the control of the sludge dewatering in which the dosage level of the coagulant can be controlled by utilizing both the CST value of sludge and the CST value of dewatering filtrate, and the CST value of the dewatering filtrate can be measured in the same manner as in the embodiment shown in FIG. 2.

Reference numeral 11 is a sludge CST measuring means which uses the same device as shown in FIG. 2, and this means 11 measures the sludge CST and then inputs the measured data into a coagulant dosage controller (12). As in the case of FIG. 1, filtrate CST data from a CST measuring means (10) for detecting the CST value of the dewatering filtrate is input into the above-mentioned controller (12), and the decrease ratio of the CST, defined below, is calculated on the basis of sludge and filtrate data, whereby the dosage level of the coagulant which is fed from a coagulant pump (6) to a sludge feed pipe (3) is controlled and the sludge is reacted with the coagulant in the coagulant reaction device (13).

Decrease Ratio of the CST (%) = (the CST value of sludge − the CST value of filtrate)/(the CST value of the sludge) × 100  (Formula 5)

The controller (12) calculates the CST decrease ratio and controls the coagulant pump (6) so that the CST decrease ratio may be maximized. The CST decrease ratio can be used in the second control method in the same way as the sludge CST in the aforesaid first control method. Thus, it is possible to optimize the coagulant dosage level by using the CST decrease ratio alone. In other words, the optimum coagulant dosage level is one which minimizes the CST decrease ratio. In this second control method, the sludge CST in addition to the filtrate CST is measured to calculate the CST decrease ratio so that the values of the CST decrease ratio better reflect the actual characteristics of the sludge, whereby accuracy of the dewatering control can be improved as compared with the first control method. To determine the relation between the CST decrease ratio and the coagulant dosage ratio, the sludge concentration is measured in the same way as described in the first control method to calculate the coagulant dosage ratio. Even if the coagulant dosage ratio is not immediately calculated, it is possible to control the sludge dewatering system by using the CST decrease ratio alone.

Figure 13:
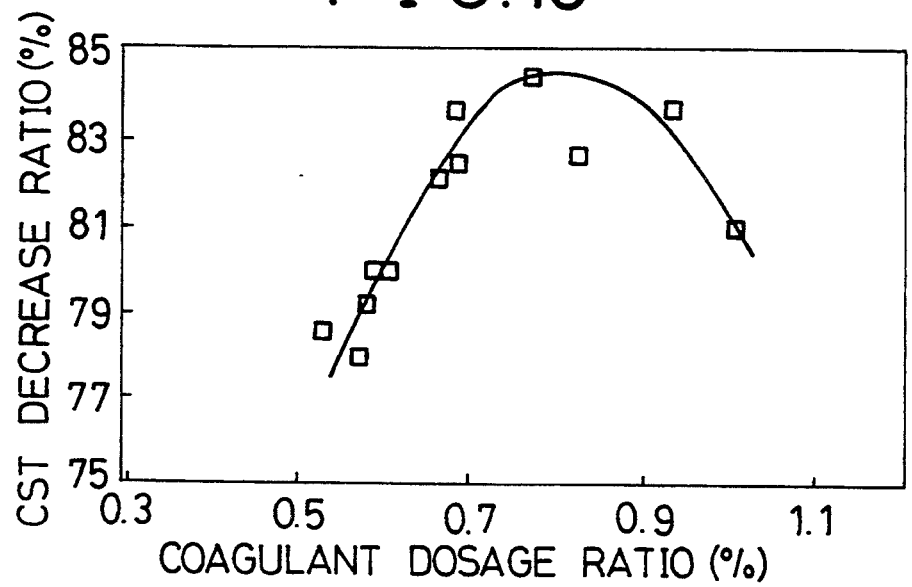
FIG. 13 shows an example of the relation between the decrease ratio of the sludge CST and the coagulant dosage ratio.

The CST decrease ratio has such a relation to a coagulant dosage ratio as shown in FIG. 13, for example, with regard to the same sludge as used for obtaining the data presented in FIG. 3.

In FIG. 13, the CST decrease ratio is maximized in the vicinity of a coagulant dosage ratio of 0.75%, and this dosage ratio is substantially in accord with the dosage ratio which permits minimizing the moisture content of the cake in FIG. 3(B).

Therefore, if the dosage ratio of the coagulant is controlled so that the CST decrease ratio may be maximized, the moisture content of the dewatered cake is minimized and the efficient coagulant dosage control can be achieved.

The control operation of this embodiment will be carried out as follows: Sludge CSTs detected by the slurry CST measuring means 11 are input into the controller (12), and the coagulant is then added to the fed sludge. After the filtrate 8 is discharged by the dehydration means 4, filtrate CSTs are measured by the filtrate CST measuring means 10. The controller 12 calculates the decrease ratios of the CST from the sludge CST values and the filtrate CST values in accordance with the above-mentioned formula 5 and then memorizes the decrease ratios.

Next, the dosage level of the coagulant is slightly increased, and after the passage of a certain time, the measurement and calculation are carried out again to obtain the CST decrease ratio. This value is compared with the previous value, and if the later value is smaller than the previous value, it can be judged that the coagulant is in excess of the optimum dosage ratio, because the decrease ratio of the CST has dropped although the coagulant has been more added. Therefore, in this case, the dosage level of the coagulant is decreased successively. In this process of successively decreasing the coagulant dosage level, when the later CST decrease ratio of the sludge containing the decreased dosage level of the coagulant become lower than the previous CST decrease ratio, it is judged that the later CST decrease ratio has dropped owing to the decrease of the coagulant amount. Therefore, the dosage level or ratio of the coagulant is increased. In this way, the CST decrease ratio is calculated at an interval of a certain time, and the dosage level of the coagulant is controlled so that the CST decrease ratio may be maximized, whereby the coagulant can be added in an optimum dosage ratio.

Incidentally, in this embodiment, there is a time lag between the measurement point of the sludge CST and the measurement point of the filtrate CST, but both the CSTs may be measured by staggering a time therebetween or if this time lag can be ignored, they may be measured simultaneously.

Furthermore, in order to save the coagulant to the utmost, it is possible to carry out the operation and control in a dosage ratio which is slightly lower than the dosage ratio which gives the maximum value of the CST decrease ratio. This is similar to the case of the above-mentioned control process based on the filtrate CST value alone.

Figure 14:
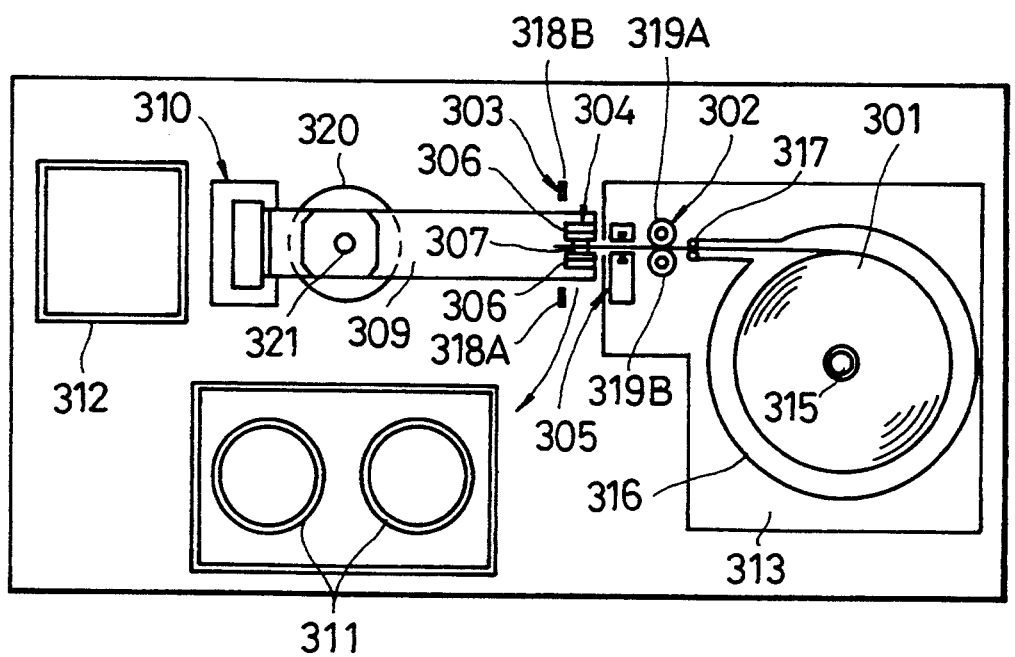
FIG. 14 shows a schematic plan illustrating another embodiment of a device for automatically measuring the capillary suction time.

FIGS. 14 and 15 show another embodiment of a CST automatic measuring apparatus.

The CST automatic measuring apparatus of this embodiment is composed of a roll type continuous filter paper (301) rotatably put on a turn table, a filter paper pulling means (302) for pulling out a certain length of this filter paper (301) at a time by a sensor device (303), a filter paper holding means (304) for holding the filter paper (301) pulled out by the filter paper pulling means (302) on both sides thereof, a filter paper cutting means (305) for cutting the filter paper (301) held by this filter paper holding means (304) into a predetermined size, three electrodes (308A), (308B) and (308C) disposed on one press surface of a pair of pressing plates (306) constituting the above-mentioned filter paper holding means (304), a rotatable support arm (309) provided with the above-mentioned filter paper holding means (304), a rising/falling means (310) for upward and downward moving this support arm (309), and sample pots (311) for receiving a sample to be measured arranged under the cut filter paper (301) which is upward and downward moved by this rising/falling means (310). Furthermore, reference numeral (312) is a filter paper disposal pot into which the filter paper (301) used for the measurement is thrown.

In the first place, the filter paper (301) which can be used in the present embodiment has a continuous roll form, as shown in FIG. 14, and it is set on the turn table (314) disposed on the base (313). In this drawing, numeral (315) is a central axis of the turn table (314), and numeral (316) is a filter paper holder which also has the function to guide the filter paper (301).

Next, the filter paper pulling means (302) is disposed in the vicinity of an outlet (317) of the filter paper holder (316), and it functions to pull out a certain length of the roll type filter paper (301) at a time by the sensor device (303) comprising, for example, a luminescence element (318A) and an acceptance element (318B). The filter paper pulling means (302) in the shown embodiment is composed of a driving roller (319A) and a pressing roller (319B) which comes in contact with the driving roller (319A) under a suitable pressure. This driving roller (319A) may have a driving source (not shown) such as a stepping motor which can stop automatically in accordance with a detection signal from the above-mentioned sensor device (303). Furthermore, the stepping motor may be constituted so as to automatically stop, when the driving roller (319A) has been rotated for a predetermined number of rotations, or alternatively a rotary axis fixed to the above-mentioned turn table (314) may be constituted so as to be directly rotated by the stepping motor or the like through a pulley and a V-belt.

When the feed of the filter paper is stopped, the filter paper holding means 304 is operated upon receipt of the stoppage signal, so that the filter paper is held on both sides thereof by the pair of pressing plates (306). Incidentally, a driving device for moving the pair of pressing plates (306) apart from and toward each other is not shown.

Next, the filter paper cutting means (305) is disposed between the filter paper pulling means (302) and the sensor device (303), and the filter paper (301) is pulled out as much as a certain length, stopped, and then cut into a certain size by a pair of cutting blades. In general, it is preferable that the filter paper (301) is cut so as to be in the form of strips (a driving portion of the filter paper cutting means is not shown). During this cutting operation, the filter paper (301) is held on both sides thereof by the pair of pressing plates (306) as described above, and therefore the paper can be cut precisely by the pair of cutting plates. Even after completion of the cutting step, the cut filter paper (301) having, for example, the strip form remains held by the filter paper holding means (304).

The pair of electrodes (308A) and (308B) are horizontally disposed on one press surface of the pair of pressing plates (306) constituting the above-mentioned filter paper holding means (304), as shown in FIG. 15, and the electrode (308C) is disposed just above the electrode (308A), it being separated from the electrode (308A) as much as a certain space. In order to stably press the filter paper strip (301), a dummy pressing lug (322) is protrusively disposed just above the electrode (308B) on a level with the electrode 308C. Furthermore, an electrode may be substituted for the pressing lug (322). Needless to say, these electrodes are electrically connected to a timer not shown.

Next, the support arm (309) provided on the tip thereof with the above-mentioned filter paper holding means (304) is rotatable by a driving device (320) such as the stepping motor or an air-actuated rotary actuator. That is, in the shown embodiment, the support arm (309) is attached to a rotary axis (321) of the driving device (320), and when this driving device (320) begins to start, the support arm (309) rotates as much as a certain angle in a clockwise direction and then stops at a predetermined position by the operation of a limit switch. Needless to say, the filter paper holding means (304) holding the filter paper strip (301) is also rotated together with the rotation of the above-mentioned support arm (309).

In the case of the shown embodiment, the rising/falling means (310) for upward and downward moving the above-mentioned support arm (309) is an air cylinder which can upward and downward move the driving device (320) itself for rotating the support arm (309), but this means (310) may be driven by means of a motor. Under the cut filter paper strip (301) which is upward and downward moved by this rising/falling means (310), the sample pots (311) for receiving a sample to be measured such as sludge are prepared. In the shown embodiment, the two sample pots (311) are provided, but needless to say, the only one pot can be provided. In addition, on the outskirt of the support arm 309, a disposal pot for the used filter papers (312) is provided adjacent to the above-mentioned pots (311).

Next, a usage example of this embodiment apparatus will be described. When a driving roller (319A) constituting the filter paper pulling means (302) begins to rotate, the roll type continuous filter paper (301) set on the turn table (314) of the base (313) is gradually pulled out from the outlet (317) of the filter paper holder (316). Afterward, when the filter paper (301) is pulled out to a position between the luminescence element (318A) and the acceptance element (318B) constituting the sensor device (303), the stepping motor which is the driving source for the driving roller (319A) is automatically stops by a detection signal from the sensor device (303).

Next, the pair of pressing plates (306) constituting the filter paper holding means (304) arranged in front of the sensor device (303) begin to close and press both sides of the filter paper (301). When the filter paper (301) is pressed by the filter paper holding means (304), an operation device for driving the filter paper cutting means (305) begins to operate, so that the filter paper (301) is precisely cut by the pair of cutting blades. After the cutting of the filter paper (301), the driving device (320) for rotating the support arm (309) provided with the filter paper holding means (304) begins to drive, whereby the support arm (309) rotates in a clockwise direction as shown by an arrow line in FIG. 14, and automatically stops at the position above the sample pot (311). The filter paper strip (301) is held on both sides thereof by the pair of pressing plates (306) constituting the filter paper holding means (304) and is rotated together with the support arm (309) to a position just above the sample pot (311), and held there.

When the rotation of the support arm (309) stops, the rising/falling means (310) begins to operate, thereby causing the support arm (309) to fall as much as a predetermined distance so that the lower portion of the filter paper strip (301) may be immersed to a certain depth into a sample of, for example, sludge in the sample pot (311). The filter paper (301) immersed to the certain depth in the sludge has hygroscopicity, and a liquid in the sludge moves upward along the filter paper (301) by a capillary suction phenomenon and reaches the pair of electrodes (308A) and (308B) disposed on the lower portion of the filter paper pressing plates (306). When the liquid of the sludge reaches the electrodes (308A) and (308B), electricity runs between these electrodes, and a timer (not shown) starts to count. The liquid of the slurry further moves upward along the filter paper (301), and when it reaches the upper electrode (308C), the count stops.

A time of from the count start to the count stop of the timer is memorized by the timer, and it can be output by a printer or the like.

In the case that an electrode is substituted for the pressing lug (322), the system should be constituted so that the count by the timer may stop when the liquid in the sludge reaches either of this electrode or the above-mentioned electrode (308C).

After completion of the measurement, the rising/falling means (310) begins to operate, and the support arm 309 provided with the filter paper holding means (304) rises to a certain height, and the support arm (309) further rotates in a clockwise direction by the driving device (320) and stops at the position above the filter paper disposal pot (312). Next, the filter paper pressing plates (306) constituting the filter paper holding means (304) provided at the tip of the support art (309) are separated from each other, so that the used filter paper (301) is allowed to fall into the filter paper disposal pot (312).

After completion of this successive operation, the support arm (309) rotates in a counterclockwise direction by the driving device (320) and returns to its original position, and it takes a stand-by state.

In this embodiment, the electrodes are disposed on the only one press surface of the pair of filter paper pressing plates constituting the filter paper holding means, but for example, the electrodes (308A) and (308B) may be provided on the one press surface and the electrode (308C) may be provided on the other press surface. Alternatively, the three electrodes may be disposed on the one press surface as in this embodiment, and other three electrodes may also be arranged at positions corresponding to the positions of the above-mentioned three electrodes on the other press surface.

The CST automatic measuring apparatus of this embodiment has the constitution and function described above, and so it can solve the problems of the conventional CST measuring apparatus using a cut filter paper. That is, according to the apparatus of the present invention, the continuous roll type filter paper having hydroscopicity is cut into a predetermined size and then used to make the measurement, and therefore the labor of replenishing the filter paper can be remarkably decreased. In addition, all the operation steps of the apparatus are automated, and thus the measurement operation can be carried out with extremely high efficiency.

As described above, according to the present invention, the CSTs of a filtrate are measured with high precision, and the dosage level of a coagulant to be added to sludge can be controlled on the basis of these values. Therefore, the sludge can be dewatered by using the coagulant in an optimum amount without any excessive addition, and a moisture content in the dewatered cake can be minimized.

In addition, when the CSTs of sludge are utilized together with the CSTs of the filtrate for the control, the optimum coagulant dosage control can be achieved, and there can be also obtained the advantage that the change in sludge characteristics such as sludge concentration can be always monitored.

Moreover, according to the present invention, the dosage level of the coagulant can be controlled with high precision simply by measuring the CSTs of the filtrate, or alternatively by of measuring both CSTs of the filtrate and the sludge.

Although the invention has been described with preferred embodiments, it is to be understood that variations and modifications may be resorted to as will be apparent to those skilled in the art. Such variations and modifications are to be considered within the purview and the scope of the claims appended hereto.

What is claimed is:

1. A sludge dewatering control system for use in a sludge dewatering plant having a coagulant addition means for adding a polyelectrolyte coagulant to the sludge and a dewatering means for dewatering the sludge which has been subjected to coagulation reactions by the addition of the coagulant, which system comprises:

a sludge concentration measuring device for successively measuring sludge concentration in a sludge feed pipe upstream from a path leading from the coagulant addition means, said concentration being calculated from any one of the following combinations: (a) temperature and capillary suction time of the sludge, (b) temperature, capillary suction time and electrical conductivity of the sludge, (c) temperature, viscosity and electrical conductivity of the sludge, and (d) temperature, viscosity, electrical conductivity and capillary suction time of the sludge, a measuring means for successively measuring the capillary suction time of filtrate discharged from the dewatering means, a coagulant feed measuring device for successively measuring flow rate of the coagulant to be introduced to the sludge feed pipe downstream from the sludge concentration measuring device, and a control means for controlling the coagulant addition means to control dosage level of the coagulant based on output from an arithmetic device, said arithmetic device successively determining a coagulant dosage, at which the capillary suction time of the filtrate is minimized, based on changes in the capillary suction time of the filtrate responsive to changes in the coagulant dosage ratio calculated from sludge concentration and coagulant flow.

2. A sludge dewatering control system for use in a sludge dewatering plant having a coagulant addition means for adding a polyelectrolyte coagulant to sludge and a dewatering means for dewatering the sludge which has been subjected to coagulation reactions by addition of the coagulant, which system comprises:

a sludge concentration measuring device for successively measuring sludge concentration in a sludge feed pipe upstream from a path leading from the coagulant addition means, said concentration being calculated from any one of the following combinations: (a) temperature and capillary suction time of the sludge, (b) temperature, capillary suction time and electrical conductivity of the sludge, (c) temperature, viscosity and electrical conductivity of the sludge, and (d) temperature, viscosity, electrical conductivity and the capillary suction time of the sludge, a measuring means for successively measuring the capillary suction time of the sludge, a measuring means for successively measuring filtrate discharged from the dewatering means, a coagulant feed measuring device for successively measuring flow rate of the coagulant to be introduced to the sludge feed pipe downstream from the sludge concentration measuring device, and a control means for controlling the coagulant addition means to control the dosage level of the coagulant based on output from an arithmetic device, said arithmetic device successively determining a coagulant dosage, at which a decrease ratio defined below is maximized, based on changes in the decrease ratio responsive to changes in the coagulant dosage ratio calculated from the sludge concentration and the coagulant flow:

*Decrease ratio (%) of capillary suction time*
$(CST) = ((\text{the CST of the sludge} - \text{the CST of the filtrate})/(\text{the CST of the sludge})) \times 100$

* * * * *